US00PP22607P3

(12) United States Plant Patent
Lord

(10) Patent No.: US PP22,607 P3
(45) Date of Patent: Mar. 27, 2012

(54) ***COPROSMA* PLANT NAMED 'JWNCOPPS'**

(50) Latin Name: *Coprosma repens*
Varietal Denomination: JWNCOPPS

(76) Inventor: John Lord, Woodbridge (GB)

( * ) Notice: Subject to any disclaimer, the term of this patent is extended or adjusted under 35 U.S.C. 154(b) by 0 days.

(21) Appl. No.: 12/802,263

(22) Filed: Jun. 3, 2010

(65) Prior Publication Data

US 2011/0061140 P1 Mar. 10, 2011

(51) Int. Cl.
*A01H 5/00* (2006.01)

(52) U.S. Cl. ..... Plt./226

(58) Field of Classification Search ..... Plt./226, Plt./263.1, 373
See application file for complete search history.

*Primary Examiner* — June Hwu
(74) *Attorney, Agent, or Firm* — Cassandra Bright

(57) ABSTRACT

A new and distinct *Coprosma repens* named 'JWNCOPPS' is disclosed, characterized by its vibrant red/purple foliage color, and shiny, narrow leaves. The new cultivar is a *Coprosma repens,* typically suited for ornamental container and landscape use.

1 Drawing Sheet

Figure 1:
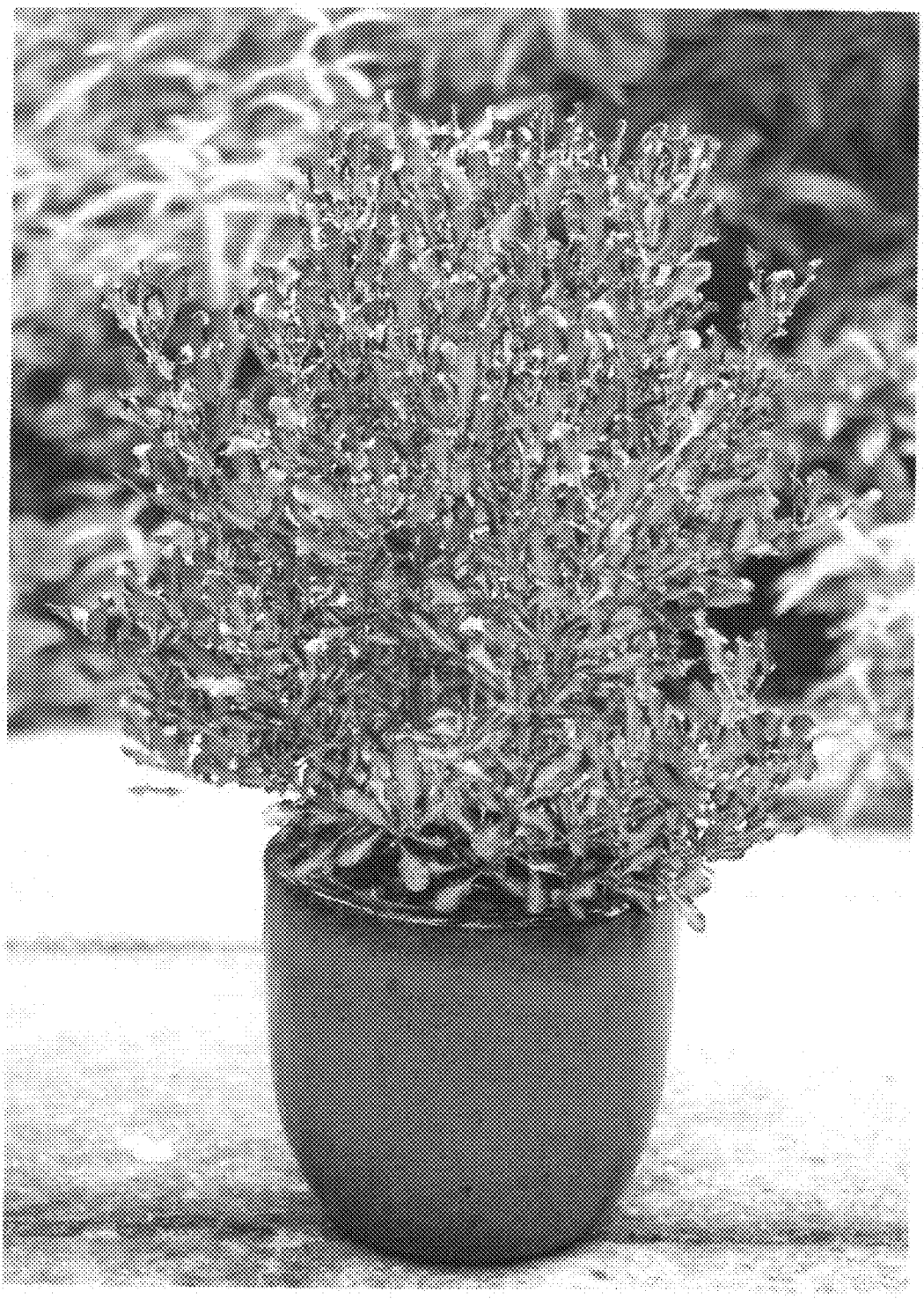

Latin name of the genus and species: *Coprosma repens.*
Variety denomination: 'JWNCOPPS'.

BACKGROUND OF THE INVENTION

The new cultivar is the result of a chance discovery in a commercial nursery in Suffolk, England. The inventor, John Lord, a citizen of England, discovered the new variety as a single branch, naturally occurring mutation growing in a commercial planting of the parent variety, the unpatented variety *Coprosma repens* 'Pacific Night.' Although unpatented in the United States, the parent variety is protected by Plant Breeder's Rights in Europe, under grant number 26069. The discovery was made in the Spring of 2006.

After selecting and isolating the new cultivar, asexual reproduction of the new cultivar 'JWNCOPPS' was first performed in the same commercial nursery by vegetative cuttings in the Fall of 2006. 'JWNCOPPS' has since produced several generations and has shown that the unique features of this cultivar are stable and reproduced true to type.

SUMMARY OF THE INVENTION

The cultivar 'JWNCOPPS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'JWNCOPPS.' These characteristics in combination distinguish 'JWNCOPPS' as a new and distinct *Coprosma* cultivar:

1. Vibrant red and greyed-purple foliage color
2. Glossy, narrow foliage.
3. Upright plant habit.

PARENTAL COMPARISON

Plants of the new cultivar 'JWNCOPPS' are similar to the parent, 'Pacific Night' in most horticultural characteristics. However, 'JWNCOPPS' differs in having brighter, more variegated foliage.

COMMERCIAL COMPARISON

Plants of the new cultivar 'JWNCOPPS' can be compared to the patented commercial variety *Coprosma* 'Fireburst' U.S. Plant Pat. No. 14,906. Plants of 'JWNCOPPS' are similar to 'Fireburst' in most horticultural characteristics, however, JWNCOPPS has darker, brighter colored foliage, with dark purple margins compared to the light pink margins of 'Fireburst.'

BRIEF DESCRIPTION OF THE PHOTOGRAPH

The accompanying photograph in FIG. 1 illustrates in full color a typical plant of 'JWNCOPPS' grown outdoors in Suffolk, England This plant is approximately 2 years old, shown in a 3 liter pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'JWNCOPPS' plants grown outdoors in Suffolk, England. Temperatures ranged from Approximately 1° C. to 8° C. at night to 1° C. to 18° C. during the day. No artificial light, photoperiodic treatments or chemical treatments were given to the plants. Measurements and numerical values represent averages of typical plant types.

Botanical classification: *Coprosma repens* 'JWNCOPPS'
Age of the plant described: Approximately 3 years.
Container size of the plant described: 3 liter commercial container.

PROPAGATION:

Time to initiate roots: Summer: 20 to 25 days at approximately 20° C.

Root description: Fine, densely branched, non-fibrous, non-fleshy

PLANT

Growth habit: Upright.
Pot size of plant described: 3 liter
Height: Approximately 50 cm from soil line to top leaf.
Plant spread: Approximately 30 cm.
Growth rate: 30 to 50 cm per year, until a mature height of 150 cm.
Stem diameter: Approximately 0.3 cm.
Stem color: New wood: Near RHS Greyed-Green 198C.
Stem color: Mature wood: Near RHS Greyed-Orange 175A.
Branching characteristics: Well-branched, bushy habit.
Length of primary lateral branches: Average 30 to 35 cm.

FOLIAGE

Leaf:
*Arrangement.*—Opposite, sessile.
*Average leaves per lateral branch.*—Approximately 10 to 20.
*Average length.*—2 to 4 cm.
*Average width.*—1 to 2 cm.
*Shape of blade.*—Oblanceolate.
*Apex.*—Obtuse.
*Base.*—Attenuate.
*Margin.*—Entire.
*Texture of top surface.*—Shiny, leathery.
*Texture of bottom surface.*—Shiny, leathery.
*Pubescence.*—Non pubescent.
*Aspect.*—Undulating margins, slight twist to overall leaf blade.
*Color.*—Young foliage upper side: Near RHS Greyed-Purple 185C, thick margin near Greyed-Purple 187A. Young foliage under side: Near RHS Greyed-Purple 185C, thick margin near Greyed-Purple 187A. Mature foliage upper side: Near RHS Greyed-Red 180A, margin near Greyed-Purple 187A. Mature foliage under side: Near RHS Greyed-Red 180A, margin near Greyed-Purple 187A.
*Venation.*—Type: Pinnate. Venation color upper side: Near RHS Greyed-Yellow 162D Venation color under side: Near RHS Greyed-Red 180A.

FLOWER

Flower type: Only male flowers observed to date. Small, polypetalus, flowers occurring in axillary umbels. Corolla described, calyx present, however, too minute to measure.
Male flower description:
*Flowers per umbel.*—10 to 20.
*Flowering season.*—Spring.
*Length of flowering.*—Approximately 2 weeks.
*Flower length.*—Approximately 0.4 cm.
*Flower width.*—Approximately 0.2 cm.
*Outer flower surface color.*—Near RHS Yellow-Green 151C.
*Inner flower surface color.*—Near RHS Yellow-Green 150C.
*Petal length.*—Approximately 0.3 cm.
*Petal width.*—Approximately 0.1 cm.
Stamens:
*Quantity.*—5.
*Filament length.*—0.3 cm.
*Filament color.*—Near RHS Yellow-Green 150C.
*Anther shape.*—Oblong.
*Anther length.*—Approximately 0.1 cm.
*Anther color.*—Near RHS Yellow 7C.
*Pollen color.*—Near RHS Black 202A.

OTHER CHARACTERISTICS

Seeds and fruits: Not observed to date.
Disease/pest resistance: Neither resistance nor susceptibility to normal diseases and pests of *Coprosma* has been observed.
Temperature tolerance: The new variety tolerates low temperatures to approximately −5° C. and has been observed to tolerate high temperatures to 30° C.

What is claimed is:

1. A new and distinct cultivar of *Coprosma repens* plant named 'JWNCOPPS' as herein illustrated and described.

* * * * *